United States Patent
de Jong et al.

(10) Patent No.: US 6,765,123 B2
(45) Date of Patent: Jul. 20, 2004

(54) PROCESS FOR THE MANUFACTURE OF MULTILAYERED WOUND DRESSINGS

(75) Inventors: Johannes H. A. de Jong, Mentor, OH (US); Roger D. A. Lipman, Oudturnhout (GB); Patrick Thomas, Turnhout (BE); Dirk I. H. Nijns, Beerse (BE)

(73) Assignee: Avery Dennison Corporation, Pasadena, CA (US)

( * ) Notice: Subject to any disclaimer, the term of this patent is extended or adjusted under 35 U.S.C. 154(b) by 303 days.

(21) Appl. No.: 10/029,105

(22) Filed: Dec. 21, 2001

(65) Prior Publication Data

US 2003/0120229 A1 Jun. 26, 2003

(51) Int. Cl.[7] ............................................. A61F 13/00
(52) U.S. Cl. ............................ 602/56; 602/43; 602/54; 602/55; 602/57
(58) Field of Search ....................... 602/41–59, 900, 602/903, 904; 128/887, 889; 604/304–308; 206/440, 441

(56) References Cited

U.S. PATENT DOCUMENTS

| | | |
|---|---|---|
| 2,862,846 A | 12/1958 | Blackford et al. |
| 3,339,546 A | 9/1967 | Chen |
| 4,192,785 A | 3/1980 | Chen et al. ................. 260/17.4 |
| 4,231,369 A | 11/1980 | Sorensen et al. ............ 128/283 |
| 4,367,732 A | 1/1983 | Poulsen et al. .............. 128/156 |
| 4,477,325 A | 10/1984 | Osburn ................... 204/159.12 |
| 4,551,490 A | 11/1985 | Doyle et al. .................... 524/22 |
| 4,622,089 A * | 11/1986 | Lauritzen ..................... 156/250 |
| 4,649,909 A | 3/1987 | Thompson ................... 128/156 |
| 4,667,665 A | 5/1987 | Blanco et al. ............... 128/156 |
| 4,693,858 A | 9/1987 | Volke ........................... 261/101 |
| 4,738,257 A | 4/1988 | Meyer et al. ................ 128/156 |
| 4,793,337 A | 12/1988 | Freeman et al. ............ 128/156 |
| 4,867,821 A * | 9/1989 | Morgan ........................ 156/152 |
| 4,884,563 A | 12/1989 | Sessions ...................... 128/155 |
| 4,952,618 A | 8/1990 | Olsen ............................ 524/17 |
| 5,133,821 A | 7/1992 | Jensen .......................... 156/245 |
| 5,632,731 A | 5/1997 | Patel ............................. 602/59 |
| 5,681,579 A | 10/1997 | Freeman ...................... 424/448 |
| 5,695,777 A | 12/1997 | Donovan et al. ........... 424/443 |
| 5,968,001 A | 10/1999 | Freeman ...................... 602/42 |
| 5,981,822 A | 11/1999 | Addison ....................... 602/41 |
| 6,103,951 A | 8/2000 | Freeman ...................... 602/48 |

FOREIGN PATENT DOCUMENTS

| | | |
|---|---|---|
| EP | 0 256 893 B1 | 6/1994 |
| EP | 0 617 938 B1 | 8/1998 |
| WO | 99/11728 | 3/1999 |
| WO | 99/14282 | 3/1999 |
| WO | 00/00132 | 1/2000 |
| WO | 00/41661 | 7/2000 |

* cited by examiner

Primary Examiner—Kim M. Lewis
(74) Attorney, Agent, or Firm—Renner, Otto, Boisselle & Sklar, LLP (57) ABSTRACT

A continuous process for manufacturing a multilayered wound dressing including an apertured wound contact layer, an absorbent material layer and a backing layer, including (a) providing a substantially continuous first web comprising the wound contact layer and a first process release liner; (b) forming a plurality of apertures through the wound contact layer; (c) applying the absorbent material layer to the wound contact layer; (d) laminating a substantially continuous web of the backing layer over the absorbent material layer to form the composite web; and (e) cutting individual multi-layered wound dressings from the composite web.

26 Claims, 4 Drawing Sheets

PROCESS FOR THE MANUFACTURE OF MULTILAYERED WOUND DRESSINGS

FIELD OF THE INVENTION

The present invention relates to multilayered wound dressings suitable for the management of especially chronic wounds. More particularly, the invention relates to the manufacture of these dressings in a continuous process such that large quantities of individual dressings can be produced in a repeatable and cost efficient manner.

BACKGROUND OF THE INVENTION

Wound dressings, and in particular, multilayered wound dressings are known to be useful in speeding healing of acute wounds, stimulating healing of chronic non-healing wounds and in reducing wound pain. Wound dressings include transparent adhesive films, primarily constructed of polyurethane, non-transparent adhesives such as hydrocolloids, semitransparent adhesives including hydrogels and non-transparent non-adhesives such as foams.

Hydrocolloid dressings have found widespread use especially for the management of chronic wounds, such as venostasis ulcers and decubitus ulcers. Hydrocolloid dressings also are useful for dressing certain acute wounds such as burns, donor sites and even post-surgical incisions. Hydrocolloid dressings are comprised of a suspension of fluid absorbent fillers in a pressure sensitive adhesive vehicle. Many hydrocolloid adhesive formulations have been described in the prior art. Suitable adhesive formulations may be found, for example, in the following patents, each of which is incorporated herein by reference in its entirety: U.S. Pat. No. 3,339,546; U.S. Pat. No. 4,231,369; U.S. Pat. No. 4,367,732; U.S. Pat. No. 4,477,325; U.S. Pat. No. 4,738,257; U.S. Pat. No. 4,551,490; U.S. Pat. No. 4,192,785; U.S. Pat. No. 4,952,618; WO 99/11728 and WO 99/14282.

Because the hydrocolloid is both adhesive and absorbent, these dressings can be placed in direct contact with the wound and can be adhered to the intact skin surrounding the wound. Generally they need no adjunct fixation and are thus convenient and economical to use. Hydrocolloid dressings are typically occlusive, which means they do not allow the wound to dry out and form eschar. Such dressings maintain the wound in a moist environment so that the cascade of cellular processes involved in wound healing proceeds in an optimal manner. Moreover, the moist hydrocolloid does not adhere to the wound. When a change of dressing is necessary the hydrocolloid dressing can be easily removed from the granulating wound bed without damaging the new tissues.

However, many chronic wounds are highly exudative, and one of the limitations of hydrocolloid dressings arises because of their relatively limited absorption capacity. If the dressing cannot absorb the wound exudate at a rate commensurate with exudate production by the wound, the dressing will quickly become saturated with fluid. This will cause the dressing to leak, and will cause maceration of the skin surrounding the wound. Wound exudate can be highly irritating to intact skin, and can cause the skin to break down and excoriate. Because these chronic wounds can often last for many months and even years, leakage of exudate can cause serious problems for the maintenance of healthy intact skin of the patient, and can therefore compromise effective wound management.

It is predominantly the older population that suffers from venostasis ulcers and decubitus ulcers. The market for dressings for these chronic wounds is therefore a growing one because of the changing demographics especially in developed countries. Considerable effort is being directed to development of improved chronic wound dressings, and this effort is very much directed to improve absorbency by use of composite dressing structures.

A number of approaches have been taken to develop dressings that have enhanced absorption capacity for chronic wounds. Dressings currently on the market that are indicated for heavily exuding wounds can comprise absorbent foams, such as absorbent polyurethane foams, or fibrous absorbents such as are used in dressings containing fibers of calcium alginate, or blends of sodium and calcium alginate, or fibers of sodium carboxymethyl cellulose. Examples of commercially available foam based dressings include Tielle®, sold by Johnson & Johnson, Allevyn®, sold by Smith & Nephew and Lyofoam®, sold by the SSL Company. Examples of fibrous dressings currently on the market include Aquacel®, sold by ConvaTec and Sorbsan®, distributed by Maersk Medical.

However, there are drawbacks with the use of these foam and fiber based dressings. Neither material is inherently adhesive and therefore the fibrous or foam pad must be held in place with adjunct fixation. The Tielle® product from Johnson & Johnson is available with the absorbent foam as an island pad centered on an adhesive coated microporous foam backing. While this dressing has a high capacity for fluid management, this capacity is achieved in part by transmission of water vapor through the microporous backing. Such water vapor transmission can lead to drying out of the wound, especially as the exudate level drops during the intermediate stage of wound healing. Drying of the wound can lead to significant delay in healing and even to deterioration of the wound bed by formation of eschar.

U.S. Pat. No. 5,981,822 addresses this problem. This patent discloses a dressing comprising a wound contact sheet laminated to one side of an absorbent layer of water swellable material such as polyurethane foam. The wound contact sheet is provided with one or more slits. Expansion of the absorbent layer by exudate absorption causes the wound contacting sheet to expand, and the slits to open, thereby allowing passage of high flow rates of exudate. If the flow of exudate falls, then the slits close, thereby avoiding excessive drying of the wound bed.

There are many other examples of composite multilayered wound dressings in the prior art. U.S. Pat. No. 4,793,337 discloses a composite dressing having an absorbent adhesive laminated to a fibrous absorbent such as an alginate. The fibrous absorbent is further laminated to a backing material such as a nonwoven polyester fabric by means of a second adhesive layer in between the fibrous layer and the nonwoven polyester fabric.

WO 00/41661 discloses a multilayered wound dressing having an absorbent layer having a high absorbency but a low lateral wicking rate and a transmission layer having a high moisture vapor transmission rate bonded to the side of said absorbent layer furthest from the wound. The wound dressing may also include an adhesive layer for adhering the dressing to the skin surrounding the wound. The optional adhesive may be a fluid interactive hydrocolloid adhesive and may be provided with perforations to assist transport of exudates through the dressing.

U.S. Pat. No. 6,103,951 discloses a composite dressing having a polymeric cover layer bonded to a fibrous web that contains a mixture of a superabsorbent and a hydrocolloid. The fibrous web is characterized by a glazed surface of fused fibers on to which are deposited particles of hydrocolloid containing adhesive. The selvage edge of the dressing is fused to itself and to the polymeric cover layer. A process for the production of such a dressing is also described.

U.S. Pat. No. 5,681,579 discloses a hydrocolloid having a polymeric support layer which can be continuous or discontinuous, an occlusive backing layer that overlies the support layer, an optional adhesive which may be a hydrocolloid adhesive on the skin contacting surface and an optional absorbent region interposed between the support and the backing layer.

EP 0 617 938 B1 discloses a wound dressing having a non-continuous hydrocolloid-containing polymeric support layer and an occlusive backing layer overlying the polymeric support layer, with an optional adhesive on at least a portion of the wound contacting surface, and an optional absorbent region interposed between the polymeric support and the occlusive layer.

U.S. Pat. No. 5,968,001 discloses a wound dressing having a wound and skin contact layer, an upper occlusive layer with an absorbent layer in between with leak prevention seals which define an absorbent region. These seals disclosed as being effective in preventing the escape of wound exudate from the dressing on to the surrounding intact skin.

It can readily be seen from the foregoing review of the prior art that there has been considerable recent activity in the development of composite wound dressings suitable for chronic wound healing. In general, these composite wound dressings contain, as elements in their preferred embodiments, both hydrocolloid adhesives and another absorbent layer such as a fibrous or foam pad, the latter acting in such a composite as a sump to contain excess exudate. Moreover, composite absorbents of hydrocolloid and foam or fiber can also be backed with a microporous foam or film. The microporous foam or film backing will transport excess moisture out of the dressing but without the concomitant risk of drying the wound bed, since the hydrocolloid adhesive will maintain the wound bed moist even if the fibrous or foam absorbent becomes overly dry through evaporation.

The wound dressings described most recently in the prior art are much more complex than those earlier described and known wound dressings. Such complexity makes development of suitable high speed processes essential so that large quantities of these more complex dressings can be manufactured economically.

SUMMARY OF THE INVENTION

The present invention relates to a continuous manufacturing process for the production of complex multilayered wound dressings comprising laminates of several dissimilar materials in which the individual materials may be combined in various, predetermined configurations. The process of the present invention is a flexible, modular continuous manufacturing process, in which any or all of the unit operations including, for example, die cutting, lamination, island pad placement, heat bonding of composite absorbents, application of release liners, may be combined in different ways to manufacture specific dressing constructions. For example, the wound contact layer of the dressing may be die cut to form slits, perforations or apertures. The absorbent layer of the dressing may be applied as a discrete island of various dimensions to the wound contact layer. With the flexible process of the present invention, the dressing construction may be heat or adhesive bonded to give integrity in use. Further, a release liner having, for example, an unfolded, single fold or double fold configuration may be provided in the continuous process of the present invention.

In one embodiment, the present invention relates to combining some or all of the foregoing operations into a single, continuous process such that the individual materials may be continuously fed into the process, and the finished dressings continuously emerge at the end of the production line. In one embodiment, the steps are carried out in a registered continuous process.

Thus, the present invention relates to a process of manufacturing a multilayered wound dressing including an apertured wound contact layer, an absorbent material layer and a backing layer, including (a) providing a substantially continuous first web comprising the wound contact layer having a first and second major face and a first process release liner adhered to the first major face of the wound contact layer; (b) forming a plurality of apertures through the wound contact layer; (c) applying the absorbent material layer to the second major face of the wound contact layer; (d) laminating a substantially continuous web of the backing layer over the absorbent material layer to form the composite web; and (e) cutting the multilayered wound dressing from the composite web, in which the steps (a)–(e) are carried out in a continuous sequence.

In one embodiment, the present invention relates to a method of manufacturing a multilayered wound dressing comprising an apertured wound contact layer, an absorbent material layer and a backing layer, including (a) providing a substantially continuous first web comprising the wound contact layer having a first and second major face, a first process release liner adhered to the first major face of the wound contact layer and the second process release liner adhered to the second major face of the wound contact layer; (b) forming a plurality of apertures through the wound contact layer by cutting, and removing the second process release liner and portions of the wound contact layer cut out from the apertures; (c) applying a discrete absorbent layer from a substantially continuous web of the absorbent material to the second major face of the wound contact layer; (d) laminating a substantially continuous web of the backing layer over the absorbent material layer to form the composite web; and (e) cutting individual multilayered wound dressings from the composite web, in which the steps (a)–(e) are carried out in a continuous sequence.

In another embodiment, the present invention relates to a method of manufacturing a multilayered wound dressing comprising an apertured wound contact layer having a first and second major face, an absorbent material layer and a backing layer, including (a) providing a substantially continuous first web comprising the wound contact layer having a first and second major face and a first process release liner adhered to the first major face of the wound contact layer; (b) forming a plurality of apertures through the wound contact layer; (c) applying a discrete absorbent layer from a substantially continuous web of the absorbent material to the second major face of the wound contact layer, cutting and removing a portion of the web of the absorbent material; (d) laminating a substantially continuous web of the backing layer over the absorbent material layer to form the composite web; and (e) cutting the multilayered wound dressing from the composite web, in which the steps (a)–(e) are carried out in a continuous sequence.

Accordingly, the method of the present invention provides a process for preparing complex multilayer wound dressings in a continuous sequence.

DETAILED DESCRIPTION

The invention will now be more specifically described with reference to the drawings, in which like reference numbers indicate like parts. The drawings are illustrative of certain embodiments of the invention, and are not intended to be limiting of the scope of the invention, which is limited only by the claims that form part of the present disclosure.

In one embodiment, the present invention relates to a method of manufacturing a multilayered wound dressing comprising an apertured wound contact layer, an absorbent material layer and a backing layer, including steps of:

(a) providing a substantially continuous first web comprising the wound contact layer having a first and second major face and a first process release liner adhered to the first major face of the wound contact layer;

(b) forming a plurality of apertures through the wound contact layer;

(c) applying a discrete absorbent layer from a substantially continuous web of absorbent material to the second major face of the wound contact layer;

(d) laminating a substantially continuous web of backing layer over the absorbent material layer to form the composite web;

(e) cutting the multilayered wound dressing from the composite web, wherein the steps (a)–(e) are carried out in a continuous sequence.

Figure 1:
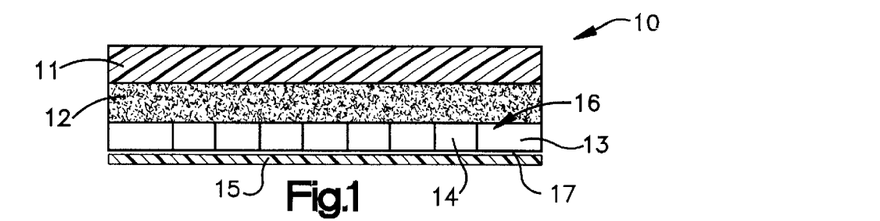
FIG. 1 is an enlarged sectional view of a typical wound dressing that can be made using the method of the present invention.

A first embodiment of a multi-layered wound dressing made by a method in accordance with the present invention is shown in FIG. 1. An individual, multi-layered wound dressing 10, is representative of one type of dressing that may be manufactured using the method of the present invention. The wound dressing 10 includes a backing layer 11, a layer of absorbent material 12 interposed between the backing layer 11 and a layer of fluid interactive adhesive 13.

The layer of fluid interactive adhesive 13 includes a plurality of apertures 14. The fluid interactive adhesive 13 is protected by the product release liner 15, which is removed prior to use. As used herein, a fluid interactive adhesive is an adhesive that absorbs exudate, while at the same time adhering the dressing to the skin surrounding the wound. Such fluid interactive adhesives are disclosed, for example, in U.S. Pat. No. 4,538,603, which is hereby incorporated by reference.

Figure 2:
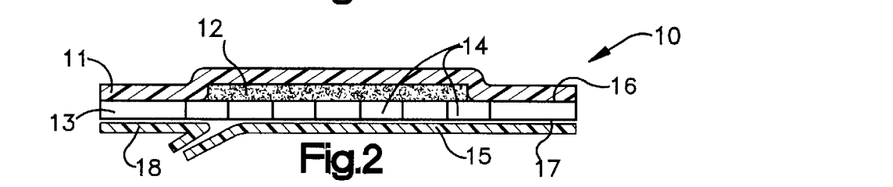
FIG. 2 is an enlarged fragmentary schematic, cross-section of one type of dressing represented in FIG. 1. that may be made using the method of the present invention.

FIG. 2 shows a cross-sectional view of one embodiment of the dressing 10 shown in FIG. 1. The embodiment shown in FIG. 2 is representative of one type of dressing that may be manufactured using the method of the present invention. The wound dressing 10 includes the same elements as in FIG. 1, i.e., a backing layer 11, a selectively shaped absorbent material layer 12, an adhesive layer 13 including a plurality of apertures 14, and further includes a two-part product release liner 15, 18. Absorbent material layer 12 is selectively bonded to a first major surface 16 of the fluid interactive adhesive layer 13. This arrangement is completely covered by the backing layer 11. The second major surface 17 of the fluid interactive adhesive layer 13 is adhered to the product release liners 15 and 18, which are removed prior to use.

Figure 3:
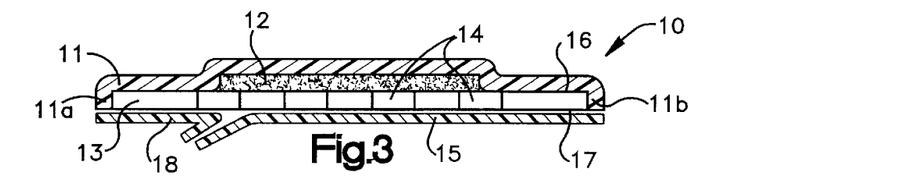
FIG. 3 is a fragmentary schematic, cross-section of an alternate embodiment of the type of dressing that may be made using the method of the present invention.

An alternative embodiment of the multilayered wound dressing 10 is shown in FIG. 3. The arrangement shown in FIG. 3 includes a backing layer 11 that includes extensions 11a and 11b. The extensions 11a and 11b provide complete coverage of the adhesive layer 13 with the backing layer 11. This arrangement helps to avoid contact with and adhesion to environmental contaminants such as dirt, dust, germs and other unwanted items that might otherwise become adhered to exposed portions of the adhesive 13.

In one embodiment, the dressings made according to the present invention are provided with a backing material that is generally occlusive, and in another embodiment may be of a porous construction such as a nonwoven fabric. Occlusive backings may be comprised of films or foams. Films such as polyurethanes and ethylene copolymers, for example, ethylene-vinyl acetate and ethylene-methyl acrylate are suitable, as are polypropylene films and polyvinylidene chloride films.

In one embodiment, the film thickness of the backing layer is in the range of from about 20 to about 500 microns. In another embodiment, the film thickness of the backing layer is in the range from about 40 to about 120 microns.

Examples of suitable foam materials are polyurethane foams, or polyethylene foams. The foam may be closed-cell or reticulated, or the cell structure may be intermediate between these two types. Film-foam laminates are also suitable. Foams of various thicknesses may be used. In general, foams up to about 1 mm thickness or more may be used. Nonwoven fabrics may be of any suitable construction.

The wound contact layer may be fabricated from any suitable material such as a polymeric or biological film, a foam, a net, a fabric or an adhesive. In one embodiment, the wound contact materials include one or more of polymeric films, polymeric nets and pressure sensitive adhesives. In another embodiment, the polymeric films include fluid interactive adhesives such as hydrocolloid adhesives, polyurethane pressure sensitive adhesives and hydrogel adhesives. In one embodiment, the wound contact layer is a hydrocolloid.

Hydrocolloid adhesives are generally first extruded or otherwise formed onto a silicone coated liner. In one embodiment the hydrocolloid is extruded or otherwise formed onto a glassine liner. This first liner performs the role of the top liner in the first step of the dressing manufacturing process. In one embodiment, the first liner has a thickness in a range from about 70 to about 160 microns, and in another embodiment, in the range from about 70 to about 90 microns. In one embodiment, the first liner has a release value in the range from about 40 and about 130 gm/25 mm width, and in another embodiment, in the range from about 60 to about 90 gm/25 mm width.

In one embodiment, a second liner is laminated over this construction. The second liner should be flexible enough to allow the total construction to be wound up with a smooth surface finish on the hydrocolloid. In one embodiment, the second liner has a release value that is not less than that of the first liner. In another embodiment, the release value of the second release liner is at least about 20 gm/25 mm width higher than the release value of the first liner. The second liner in one embodiment may be a film of high-density polyethylene with one or both of its sides siliconized. In one embodiment, the second liner may have a thickness in the range from about 50 to about 100 microns, and in another embodiment, a thickness in the range from about 60 to about 80 microns. In one embodiment, the second liner has a release value in the range from about 60 to about 120 gm/25 mm width, and in another embodiment, in the range from about 70 to about 100 gm/25 mm width.

Other liners may be utilised to replace either or both of the aforementioned liners so long as the relationship between the two liners and the tooling remains the same. By this it is meant that (a) the tooling is made to reflect the thickness of the liners used and (b) the differential release value between the liner on which the hydrocolloid adhesive is extruded (preferably the top liner in the dressing manufacturing process) and the liner that is laminated to the other side of the hydrocolloid is greater than zero and in one embodiment at least about 20 gm/25 mm width.

The absorbent material layer can be made of any material suitable for wound care that can absorb body fluids. Materials that may be used include fabrics, foams, fibrous structures of polyester, polypropylene, polyethylene and the like. Other suitable materials include as non-limiting examples natural and synthetic polymeric absorbents, superabsorbents and cellulosics. Fibrous absorbents manufactured from absorbent fibers such as alginate fibers and sodium carboxymethyl cellulose fibers, otherwise referred to as hydrofibers, are particularly useful. Composite materials that can direct the flow of the exudates, such as the blends of textile and gel-forming fibers laminated to a spreading layer of viscose polyester scrim described in WO 00/41661, the disclosure of which is hereby incorporated by reference, may also be employed.

As used herein, the term "substantially continuous" means, with respect to a component of the process, for example the backing layer of the dressing, such component is provided in a long, continuous condition, such as on a supply roll, from which a plurality of parts may be obtained. The term "substantially" is included in recognition of the fact that a given supply roll must have a finite length. With respect to a process, the term "substantially continuous" is used in its conventional meaning, and means that the operation(s) is/are carried without significant interruption or cessation between steps.

Figure 4:
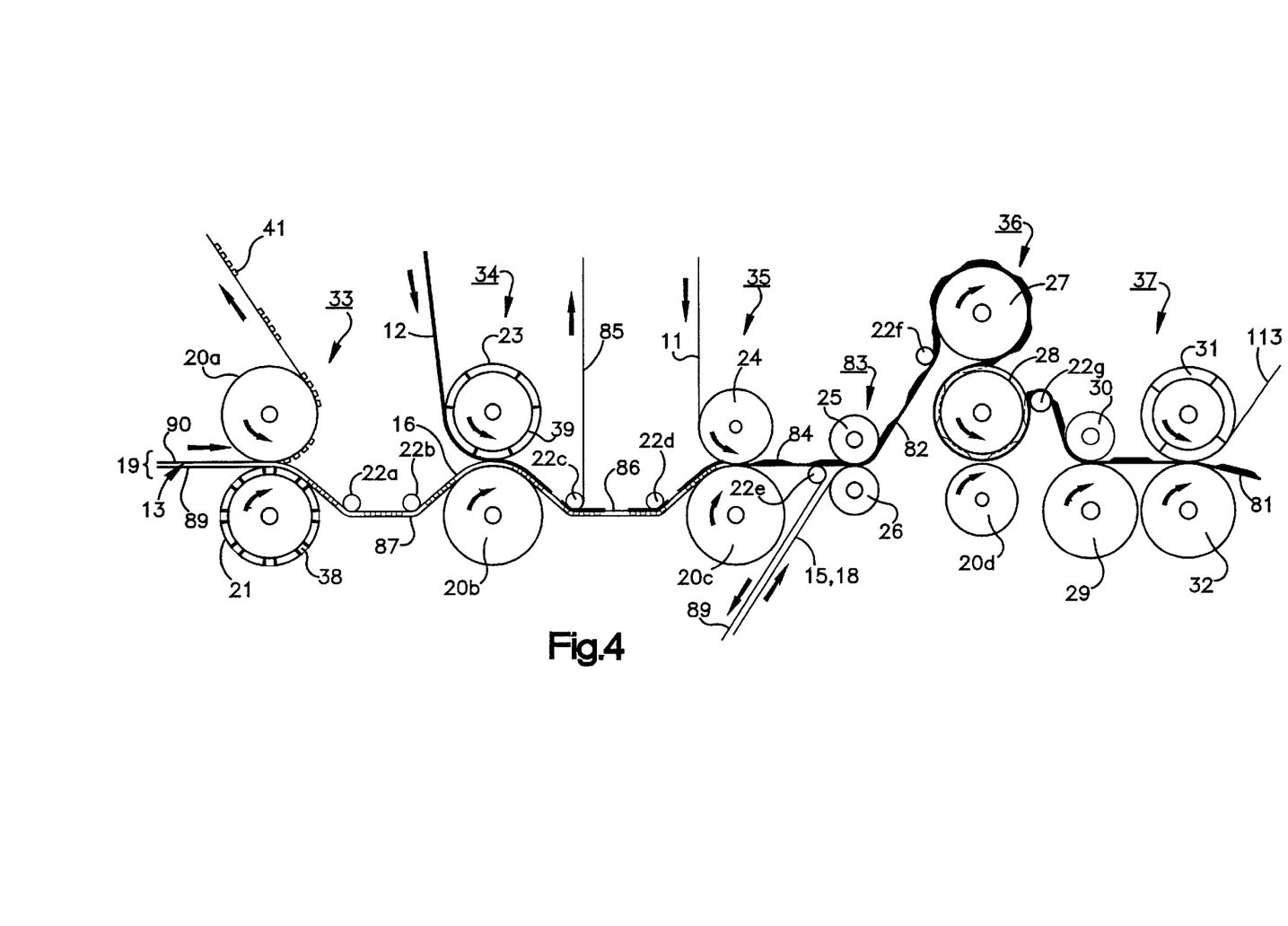
FIG. 4 schematically shows one embodiment of an apparatus for carrying out the method of the present invention.
Figure 5:
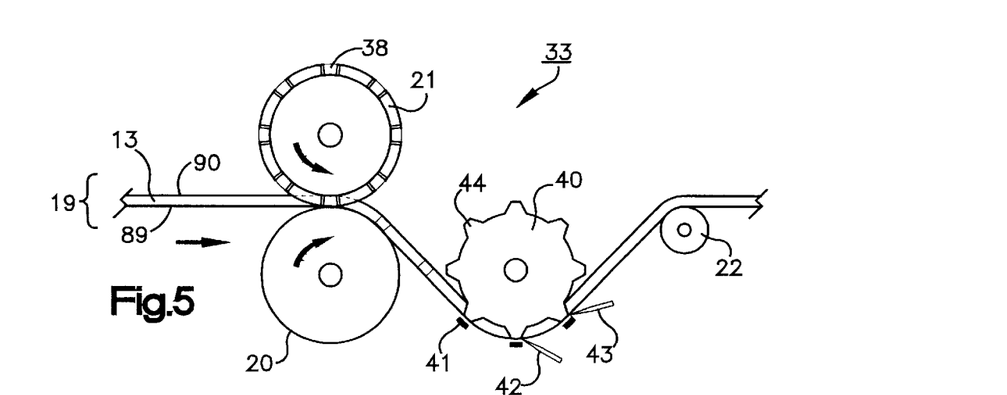
FIG. 5 schematically shows an alternative embodiment of the aperture formation aspect of an apparatus for carrying out the method of the present invention.
Figure 7:
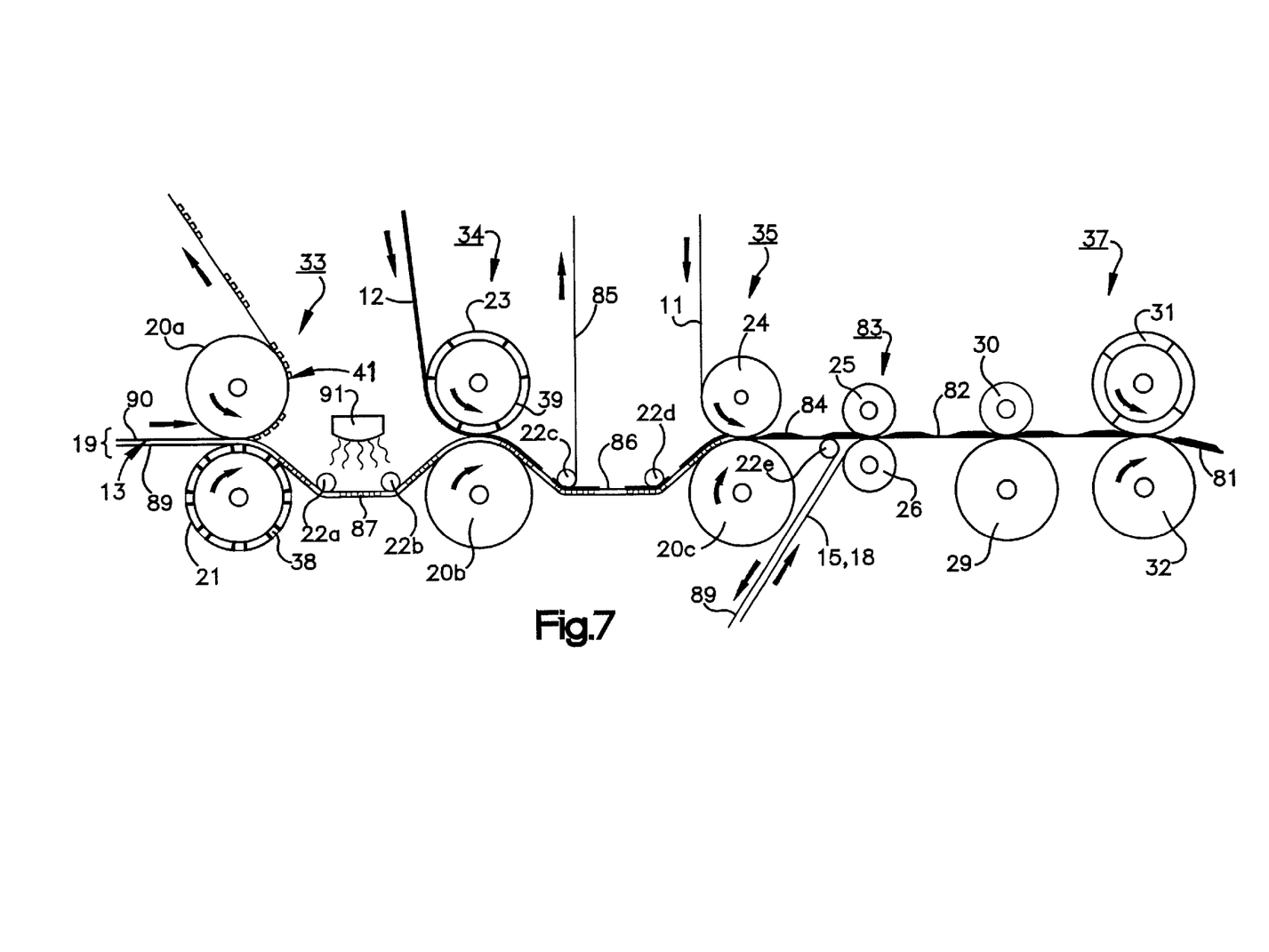
FIG. 7 schematically shows an alternate embodiment of the apparatus for carrying out the method of the present invention.

The following is a general description of the process with reference to FIGS. 4, 5 and 7. The unit operations in the manufacturing process will be described in turn. The method of the present invention provides a substantially continuous method of manufacturing a multilayered wound dressing. In one embodiment, the steps are carried out in a registered continuous sequence, in which the individual steps are conducted in a single, continuous process and the steps are simultaneously performed in registration with each other and including substantially no breaks or accumulation of parts between the steps. The specific materials mentioned in the following description are exemplary only, and are provided by way of illustration, not of limitation.

Referring initially to FIG. 4, there is shown an embodiment of an apparatus for carrying out the method of the present invention. In the first step, there is provided, from a supply roll (not shown), a substantially continuous first web 19 which includes the wound contact layer 13 and a first process release liner 89 adhered to a first (or bottom) major face of the wound contact layer. In this embodiment (shown in FIG. 4), the first web includes a second process release liner 90 adhered to a second (or top) major face of the wound contact layer 13. Suitable materials for the wound contact layer are disclosed above. In one embodiment, the first process release liner 89 is high density polyethylene, and the second process release liner 90 is glassine paper.

In the second step of the process a plurality of apertures 14 are formed through the wound contact layer 13. In one embodiment, the apertures 14 are die cut. The substantially continuous first web 19 including the a wound contact layer 13 enters the first die cut station 33 with the first process release liner 89 on the bottom and the second process release liner 90 on top. In one embodiment, the apertures are formed by kiss die cutting.

Apertures 14 are cut into the wound contact layer 13 in the web 19 by means of a hardened steel rotary tool 21 cutting against a hardened steel anvil roller 20a, the web 19 passing in between the tool 21 and the anvil roller 20a. As a result, aperture waste pieces 41 are formed, which are then disposed of suitably. The tool 21 is designed specifically to achieve selected and predetermined size, shape, and spatial arrangement of the apertures 14. The tool 21 is further designed to cut though the first process release liner 89 and the hydrocolloid 13, but not through the second process release liner 90.

In one embodiment, the cavities 38 of the tool 21 are filled with a plug material 38a to prevent the aperture waste pieces 41 from remaining in the tool 21. The plug material 38a should be of a density that enables the plug 38a to compress while under pressure and to return to its original shape following the release of the pressure. The thickness of the plug material 38a depends on the tool design and should be such that it prevents the aperture of the first process release layer 89 and the wound contact layer 13 from remaining in the tool 21 following the cutting of the aperture. The plug material 38a may be made of any material deemed suitable, for example from polyethylene foam.

In one embodiment, the aperture waste pieces 41 are removed from the web 19 by removing the second process release liner 90 to which the aperture waste pieces are adhered. The angle of delamination is, in one embodiment, between 0 and about 180°. In another embodiment, the angle is between about 10 and about 90°, and in another embodiment, the angle is between 20 and about 60°. In one embodiment, the differential release between both liners 89 and 90 and the wound contact layer 13, disclosed above as between zero and about 20 gm/25 mm width, should be such that they overcome the tendency of the aperture waste 41 to remain in the web 19. In other words, the release strength between the adhesive 13 and the second process release liner 90 should be sufficiently strong to assure that the aperture waste pieces 41 are removed with the liner 90, while the wound contact layer 13 remains adhered to the first process release liner 89. In one embodiment, an idler 22*a* assists in controlling the angle of separation of the second process release liner 90 from the web 19. The aperture waste pieces 41 proceed, along with the top liner 90 to a collection point (not shown).

If the wound contact layer 13 is a material other than a fluid interactive adhesive, for example, a film wound contact sheet as specified in U.S. Pat. No. 5,981,822, means to establish an initial bond between the contact layer and the absorbent material layer may be required before proceeding to the next process step. In one embodiment, described below with reference to FIG. 7, the process includes a heating apparatus to accomplish this adhesion. In an alternate embodiment, the film wound contact sheet may be sprayed with, for example, a hot melt adhesive such as ethylene-vinyl acetate copolymer followed by compression with a heated roller to activate the adhesive.

Following the removal of the second process release liner 90 and the aperture waste pieces 41 the resultant web 87, which includes a selectively apertured wound contact layer 13 and the first process release liner 89, web 87 proceeds to the absorbent layer application operation.

In one embodiment shown in FIG. 4, the web 87 passes around a pair of idlers 22*a* and 22*b*. As noted above, the idler 22*a* assists in separation of the second process release liner 90 from the web 87. The idler 22*b* assists in maintaining an optimum angle of approach to the second unit.

In the next step, the absorbent material layer 12 is applied to the second major face of the wound contact layer 13. In one embodiment, this step is carried out at a second die cutting station 34. At the die cutting station 34, a continuous web of the absorbent material layer 12 is applied to the first major face 16 of wound contact layer 13 and is cut into a predetermined shape. As noted above, in one embodiment, the absorbent material layer 12 may be a hydrofiber material.

In one embodiment, a hardened steel rotary tool 23 cuts the absorbent material from the top against a hardened steel anvil roller 20*b*. In one embodiment, the tool 23 has an angle of cut specific to material used for the absorbent material 12 and a cutting depth specific to the material used in the wound contact layer 13 on the bottom liner 89. In one embodiment, the rotary tool has been specifically shaped to achieve a predetermined shape of the absorbent material layer applied to the first major surface of the wound contact layer 13.

The rotary tool 23 includes cavities 39 which are defined by the cutting edges of the tool. The cavities 39 and the cutting edges cut the absorbent material to a desired shape and size, and generate a waste matrix 85. As the web exits the second die station 34 the waste matrix 85 is removed. In one embodiment, removal of the waste matrix 85 is assisted by passing the web around an idler 22*c*. The waste matrix 85 is conveyed to a removal system (not shown).

In one embodiment, the cavities 39 of the tool 23 are plugged in order to apply a small amount of pressure between the surface of the wound contact layer surface and the shaped absorbent material, encouraging it to remain in place during the removal of the matrix waste 85. In one embodiment, the plug material has a density in the range from about 60 to about 200 kg/m$^3$. The density of the plug is selected to enable the plug to compress while under pressure (i.e., during the cutting and shaping of the absorbent material) and then to return to its original shape following the relief of the pressure.

Removal of the waste matrix 85 leaves a web 86 including specifically shaped and placed pieces of the absorbent material 12 on the upper side of the layer of the specifically apertured wound contact material 13. In one embodiment, the absorbent material layer 12 is applied to overlap the plurality of apertures in at least one area of overlap. Thus, in one embodiment, the absorbent material layer 12 is a selectively sized and shaped, but relatively elongate sheet, which covers both the apertures 14 and the remaining portions of the wound contact layer 13. The absorbent material layer 12 and the wound contact layer 13 are supported on the first process release liner 89. This resultant web 86 then goes on to the next operation. In one embodiment, en route to the next processing station, the web 86 passes around an idler 22*d*. The idler 22*d* assists in orienting the web 86 towards the third unit.

In the next, a substantially continuous web of the backing layer 11 is laminated at a third die station 35 over the absorbent material layer 12 and the wound contact layer 13 to form a composite web 84. Composite web 84 includes the apertured wound contact layer 13, the absorbent material layer 12 and the backing layer 11.

In one embodiment, the lamination is carried out by passing the web 86 and the backing layer through the nip of a hardened steel anvil roller 20*c* and a flexible rubber-covered steel laminating roller 24. The "rubber" covering may be a silicone rubber, high density polyethylene or any other suitable flexible plasticized polymer. In one embodiment, the flexible surface of the laminate roller has a hardness greater than about 50 Shore A, and in another embodiment, the hardness is above about 70 Shore A. In one embodiment, the laminating pressure is desirably kept to a minimum, for example, not more than 6 bar abs. In one embodiment, the laminate roller 24 includes a relief structure along its peripheral surface.

In one embodiment, the backing layer 11, which may be a film or a foam as described above, is coated with a tie layer of adhesive. The adhesive may be, for example, a medical grade acrylic pressure sensitive adhesive. In one embodiment, the adhesive is the same adhesive used for the wound contact layer 13. In one embodiment, the backing layer 11 may be supported on a removable liner shown as 114 in FIG. 8A described below. In one embodiment, the backing layer is unwound at the lowest possible tension, for example, less than about 20N. In another embodiment, the tension is less than about 10N. In an embodiment including a backing liner, the backing liner is removed in such a manner so as to avoid stretching of the unsupported film/foam layer prior to it being laminated.

In the next step of the process, the first process release liner 89 of composite web 84 is replaced with a product release liner 15. In one embodiment, the product release liner includes two parts 15 and 18, as shown in FIG. 4.

In one embodiment, as shown in FIG. 4, the first process release liner 89 is removed from the composite web by passing the liner 89 around an idler 22*e*, having a predetermined diameter. In one embodiment, the idler 22E has a diameter in the range from about 50 to about 80 mm. The idler 22E facilitates the removal of liner 89. The resultant web then travels to a laminating nip 83, which includes a rubber covered steel pressure roller 25 and a steel back-up roller 26, the product release liner(s) 15 (18) are introduced to the composite web 84. In one embodiment, the rubber covering the pressure roller 25 has a hardness greater than about 50 Shore A, and in another embodiment, the hardness is greater than about 70 Shore A. In another embodiment, the laminate roller 25 includes a relief structure along its peripheral surface. In one embodiment, as shown in FIG. 4, the liner replacement step further includes passing the product release liner(s) 15(18) and the web through a nip defined by the rollers 25 and 26.

As noted above, the product release liners may be of any suitable design, for example one-piece 15 or two-piece 15,18 with one of the liners having a fold, to ease the removal of the said liner system by the end user. In one embodiment, a three-piece liner is used. Non-limiting examples of suitable liner systems are shown in FIGS. 1, 2 and 3, and have been described above. The composite web 84, including the product release liner 15(18), may be referred to as a second composite web 82.

Referring still to FIG. 4, the second composite web 82 is passed from laminating nip 83 through a heating zone. The heating zone is comprised within calendaring station 36. Alternatively, the heating step is carried out at another point in the process. In one embodiment, the heating step is omitted as unnecessary, because of the particular adhesive employed.

In the embodiment shown in FIG. 4, the second composite web 82 enters the calendaring station 36 by first passing around an idler 22f, which assists in causing the web 82 to wrap around a top roller 27. In one embodiment, the top roller 27 is heated. The web 82 passes around the top roller 27 and then proceeds to pass through the nip between the top roller 27 and a middle roller 28, and then around the middle roller 28. In one embodiment, the middle roller 28 is heated. In one embodiment, both the top roller 27 and the middle roller 28 are heated. The second composite web 82 passes around the middle roller 28 and through the nip between the middle roller 28 and a hardened steel anvil roller 20d. In the embodiment shown in FIG. 4, contact between the second web 82 and the middle roller 28 is maintained and assisted by an idler 22g. As a result of passing through the calendaring station 36, the wound contact layer 13 is bonded to the absorbent material layer 12 in the at least one area of overlap between these layers.

In one embodiment, the heated roller 27 has a predetermined diameter, and the heated roller 28 has a different, also predetermined, diameter. In this embodiment, the difference in the predetermined diameters is controlled by hardened steel bearer rings (not shown), The difference in diameters creates an air gap between the two rollers 27 and 28 through which the web 82 passes. The specific air gap, temperature and speed of the web through the calendaring station 36 enables the selection of specific bonding properties between the absorbent material layer 12 and the first major surface 16 of the wound contact layer 13.

In one embodiment, both the pressure at the nip between the top roller 27 and the middle roller 28, which is defined and controlled by the gap in the nip, and the temperature of the rollers 27 and 28, are important to determining the bonding between the absorbent material layer 12 and the wound contact layer 13. Of course, the nature of any adhesive used to bond these layers is also important. By selection and manipulation of these variables the nature of the bond between the absorbent material layer 12 and the wound contact layer 13 can be varied and controlled.

In one embodiment, the gap between the rollers 27 and 28 is less than about 1 mm, and in another embodiment is between about 0.6 and about 0.9 mm. In general, the gap is fixed for a specific set of product components.

In one embodiment, the gap between the rollers 27 and 28, and the temperature of rollers 27 and 28 are adjusted so that the pressure at the nip between the rollers 27 and 28 is sufficiently high to drive the fibers of the absorbent material layer 12 into fluid interactive adhesive 13, such that fibers appear at the surface of the wound contacting layer 13. This embodiment produces a composite absorbent material that is able to wick wound exudate and is thereby able to increase the rate of exudate absorption. In this embodiment, forming apertures in the wound contacting surface is not necessary to achieve acceptable absorption.

In one embodiment, the operating temperature of the surface of the heated rollers 27 and/or 28 is in the range from about 80 to about 130° C., and in one embodiment from about 90 to about 120° C. Dwell time, i.e., the time the second composite web 82 is in contact with the heated surfaces, is defined by the line speed, the diameter of the rollers 27 and 28 and the specific web path around them. In one embodiment, the dwell time is usually in the range from about one to about 15 seconds. The calendaring station 36 is not limited as to the number of heated rollers. In various embodiments, from zero to three or more heated rollers can be incorporated in order to cooperate with the line speed for the other steps of the process, and hence throughput of the process of the invention may be controlled. In one embodiment, by appropriate selection of the adhesive, the calendaring station 36 uses no heated rollers.

Referring still to FIG. 4, in the next process step, individual multilayered wound dressings 81 are cut from the second composite web 82. In one embodiment, the dressing 81 is cut from the composite web 82 by die-cutting.

As the second composite web 82 proceeds to this final cutting station 37, it passes through an outfeed nip formed by a pressure roller 30 and a knurled roller 29 before it is die cut. In another embodiment, the pressure roller 30 is a rubber covered steel pressure roll. In one embodiment, the rubber covering the pressure roller 30 has a hardness greater than 50 shore A, and in another embodiment, the rubber has a hardness of greater than 70 shore. In one embodiment, the pressure roller 30 includes a relief structure along its peripheral surface. The outfeed nip helps to keep the web under tension and transport it to the cutting station 37.

In one embodiment, the final cutting is performed from above the web by a hardened steel rotary tool 31 that is shaped specifically to the shape of the final patch of the multilayered wound dressing. The tool 31 forms a nip and cuts against a hardened steel anvil roller 32. The patches of the multilayered wound dressing are delivered from the process on a conveyor belt (not shown). The resultant waste matrix 113 is conveyed to a collection means (not shown).

The rollers of the first 33, second 34, third 35, final 37 die cut stations, the heated calendaring station 36 and the laminating station 83 are all driven in a timed and synchronous manner that allows the die cutting and laminating required to achieve the multilayered wound dressings 81. The co-rotational action of these driven rollers transports the web through the machine. This timed relationship is adjustable for each individual station. The timing can be by any means deemed suitable.

In the following, several alternative embodiments are shown and described. Where similar parts perform similar operations as described above with respect to the embodiment of FIG. 4, the description thereof is not repeated.

Referring now to FIG. 5, an alternative embodiment of the first die cut station 33 is shown. As in the embodiment of FIG. 4, a web 19, including a wound contact layer 13, a first process release liner 89 and a second process release liner 90, is provided to the first die cutting station 33. Die cut station 33 includes a hardened steel anvil roll 20 and a hardened rotary steel tool 21. The rotary tool 21 is specifically shaped to form a desired shape in the aperture 14 in the wound contact layer 13. The rotary tool cuts through the backing liner 89, through the hydrocolloid adhesive layer 13 and through the thin release liner 90.

In the embodiment shown in FIG. 5, the second process release liner 90 is not removed with the aperture waste pieces 41. Instead, the aperture waste pieces 41 are removed from the web by use of a counter roller 40 and at least one pre-positioned blade 42. As shown in FIG. 5, two pre-positioned blades 42 and 43 may be used. The counter roller 40 may be made from aluminum, or may be made from suitable plastic materials, as well as from various metals. The counter roller 40 includes a plurality of nodules 44 on its outer surface. The nodules 44 form a complimentary positive of the negative of the cavities in the rotary tool 21. The nodules 44 are of a predetermined size slightly smaller than the aperture waste pieces 41. As the counter roller 40 rotates the aperture waste pieces 41 are pushed out by the nodules 44 and are removed by the pre-positioned blades 42 and 43. The blades 42 and 43 act to remove the waste pieces 41, for example, by scraping them off the web after the waste pieces are pushed through the web by the nodules 44.

Figure 6:
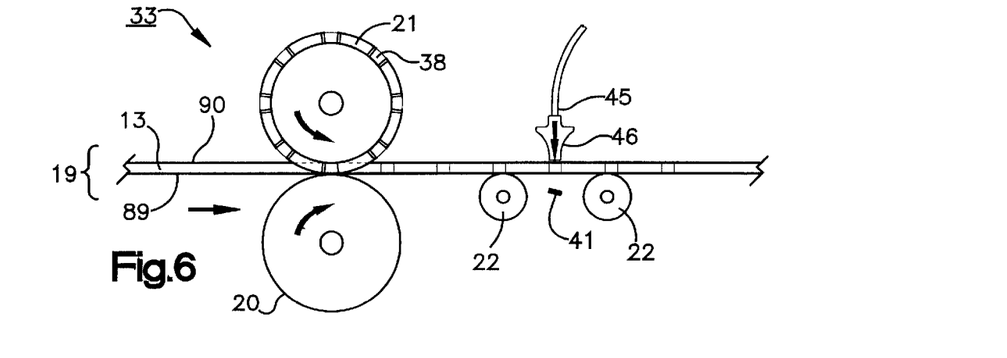
FIG. 6 schematically shows another alternative embodiment of the aperture formation aspect of an apparatus for carrying out the method of the present invention.

FIG. 6 shows a further alternative embodiment of the first die cut station 33. The die cut station 33 embodiment shown in FIG. 6 comprises a hardened steel anvil roll 20 and a hardened rotary steel tool 21 as described in the embodiment of FIG. 5, in which the web 19 is cut through its entire thickness, including through the first process release liner 89.

In the embodiment of FIG. 6, the aperture waste pieces 41 are removed from the web 19 by applying a jet of compressed air from compressed air source 45 to the web through a nozzle 46. The nozzle 46 has a predetermined shape, size and internal taper, and the air has a predetermined pressure and flow rate to provide air of sufficient force to remove the aperture waste pieces 41 from the web 19. A pair of idlers 22 is arranged on either side of the nozzle 46 at a predetermined distance apart. The idlers 22 assist in removal of the aperture waste pieces 41 by keeping the web 19 under tension.

In addition to the foregoing means for removing the aperture waste pieces 41, other means for such removal known in the art may be used as appropriate.

FIG. 7 shows an alternative embodiment of the process of the present invention which uses a radiant heating means in place of, or in addition to, the contact heating means described above. In this embodiment, the web 19 is heated by at least one heat-emitting device 91, which is remote from the web. Thus the heat is not applied by contact heating, as in the calendaring station 36 shown in FIG. 4. This heating method is particularly useful when the wound contact layer comprises a material other than a fluid interactive adhesive. For example, the wound contacting layer may comprise a film onto which an adhesive has been applied. This heating method may be used to activate the adhesive that has been applied to film. The heating mechanism can be infrared or any other means deemed suitable The heating provides activation for the adhesive from which the wound contact layer 13 is formed, and facilitates attachment of the absorbent material layer 12 thereto. The subsequent process step is then carried out, substantially as described above with respect to the embodiment shown in FIG. 4. In another embodiment, the heating means is in direct contact with the web.

As shown in FIG. 7, the resultant web 84 is transported to a laminating station 83 including a steel back-up roller 26 and a laminating roller 25 having a steel core and a rubber covering, substantially the same as in the embodiment shown in FIG. 4. As described above, the rubber covering may be, for example, a silicone rubber and may have a predetermined Shore hardness. The product release liner(s) 15 (18) are laminated to the web 84 at the laminating station 83.

Having exited the laminating station 83 the resultant web 82 is transported to the final die cut station 37. The final die cut station comprises a knurled roller 29 and pressure roll 30 transporting the web 82 to the hardened steel anvil roller 32 and the hardened steel rotary tool 31. The rotary tool 31 has been specifically shaped to cut the final multilayered wound dressing patch 81 from the web.

In this embodiment, as in the embodiment shown and described with respect to FIG. 4, the rollers of the first 33, second 34, third 35 and final 37 die cut stations, and the laminating station 83 are all driven in a timed and synchronous manner that allows the die cutting and laminating required to achieve the multilayered wound dressings 81. The co-rotational action of these driven rollers transports the web through the machine. In this embodiment, as in all embodiments of the present invention, the timed relationship among the elements of the apparatus is adjustable for each individual station. The timing can be by any means known in the art that is deemed suitable.

Figure 8:
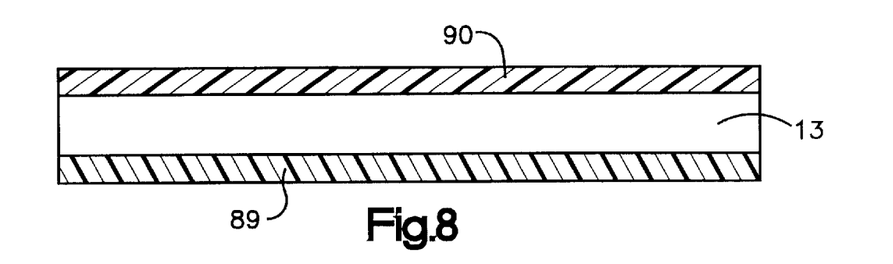
FIGS. 8 and 8A schematically show sectional views of fluid interactive layers used in the method of the present invention.

FIG. 8 shows a representation of the wound contact layer 13 interposed between a first process release liner 89 and a second process release liner 90. In one embodiment, the release liner 89 has at least one of its sides siliconized, or otherwise treated to provide a similar release property. The release liner 89 has a predetermined release property. In one embodiment, the second release liner 90 has a predetermined release property that is lower than the predetermined release property of the first release liner 89. In one embodiment, the second release liner has at least one side siliconized or otherwise treated to provide a similar release property.

Figure 8A:
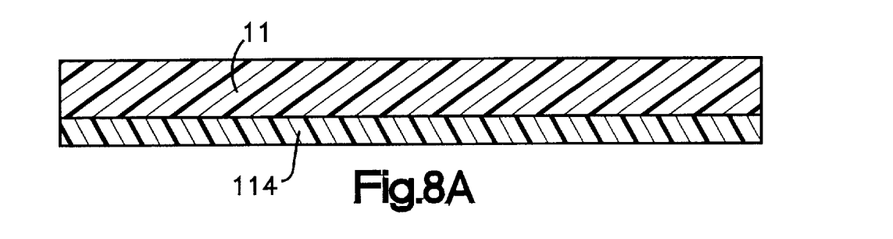

FIG. 8A shows an embodiment of the backing layer 11 in which a removable release liner 114 is adhered. In one embodiment, the backing liner shown in FIG. 8A includes an adhesive layer applied to the backing layer 11 and covered by the release liner 114. The adhesive may be any known adhesive as appropriate to the present invention.

Figure 9:
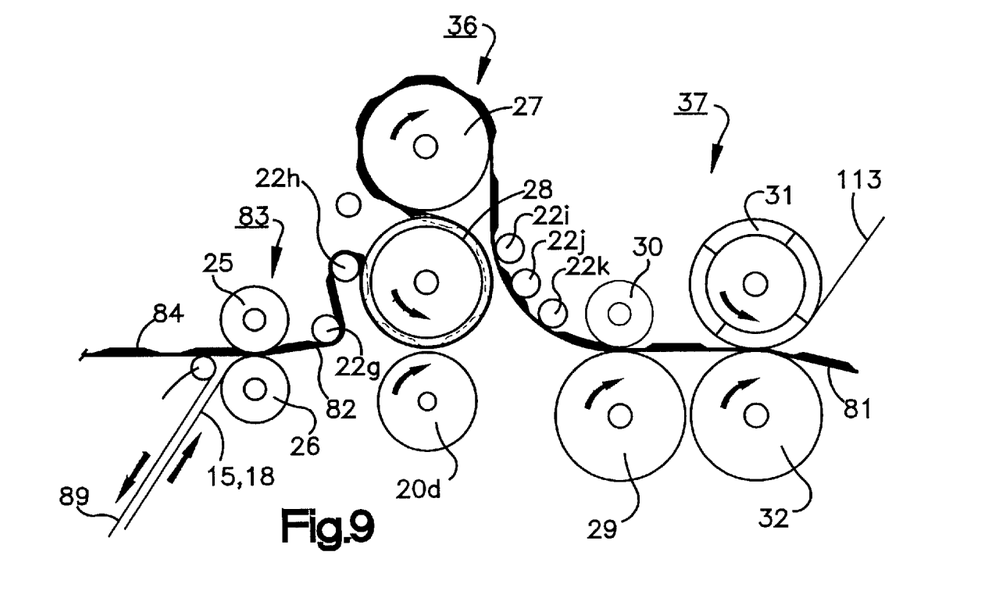
FIG. 9 schematically shows an alternate embodiment of the calendaring aspect of an apparatus for carrying out the method of the present invention.

FIG. 9 shows an alternative embodiment of the calendaring station 36. In this embodiment, the composite web 82 enters the calendaring station 36 by first passing around a pair of idlers 22G and 22H, which assist in causing the web 82 to wrap around a middle roller 28. In one embodiment, the middle roller 28 is heated. As the web 82 passes around the middle roller 28, it passes through a nip formed by the middle roller 28 and a bottom hardened steel anvil roller 20D. The web 82 continues around the middle roller 28 and then proceeds to pass through a nip between the middle roller 28 and a top roller 27. The web 82 then continues around the top roller 27. In one embodiment, the top roller 27 is heated. In one embodiment, both the top roller 27 and the middle roller 28 are heated. The second composite web 82 passes around the top roller 27 and then around a series of idlers 22I, 22J and 22K. Contact between the web 82 and the rollers 27 and 28 is maintained and assisted by the plurality of idlers 22H–22K.

The relationships between the rollers 27 and 28 and the roller 20D, in particular, the relative diameters, the temperatures and the relative speeds of rotation are similar to those described above with respect to FIG. 4. The relationships between these parameters are similar, and the parameters may be similarly manipulated to control operation of the calendaring station 36.

While these particular embodiments of an improved method have been shown and described, it is to be understood that the invention is not limited only to these, and protection is sought to the extent defined by the following claims.

What is claimed is:

1. A method of manufacturing a multilayered wound dressing comprising an apertured wound contact layer, an absorbent material layer and a backing layer, comprising:
   (a) providing a substantially continuous first web comprising the wound contact layer having a first and second major face and a first process release liner adhered to the first major face of the wound contact layer;
   (b) forming a plurality of apertures through the wound contact layer;
   (c) applying a discrete absorbent material layer from a substantially continuous web of the absorbent material layer to the second major face of the wound contact layer
   (d) laminating a substantially continuous web of the backing layer over the absorbent material layer to form the composite web; and
   (e) cutting individual multilayered wound dressings from the composite web,
wherein the steps (a)–(e) are carried out in a continuous sequence.

2. The method of claim 1, wherein in step (b) the plurality of apertures are formed by die cutting.

3. The method of claim 2, wherein the first web further comprises a second process release liner adhered to the second major face of the wound contact layer.

4. The method of claim 3, further comprising simultaneously removing the second process release liner and portions of the wound contact layer die cut from the apertures.

5. The method of claim 2, wherein step (b) further comprises removing portions of the wound contact layer cut out from the apertures by applying an external force to the portions.

6. The method of claim 1, wherein the absorbent material layer is applied in step (c) to overlap the plurality of apertures in at least one area of overlap.

7. The method of claim 1, further comprising removing the first process release liner and applying a product release liner.

8. The method of claim 7, wherein the product release liner comprises a two-part release liner.

9. The method of claim 1, further comprising heating the composite web.

10. The method of claim 9, wherein the step of heating comprises contacting the composite web with at least one heated roller.

11. The method of claim 10 wherein the at least one heated roller is maintained at a temperature between about 80° and about 130° C.

12. The method of claim 10, the composite web is contacted with at least two heated rollers.

13. The method of claim 9, wherein the step of heating comprises applying a remote heat source to heat the composite web.

14. The method of claim 9, wherein the heating step follows step (b).

15. The method of claim 9, wherein the heating step follows step (e).

16. The method of claim 1, wherein the step (e) further comprises passing the composite web through the nip of a knurled roller and a pressure roll.

17. The method of claim 1, wherein the wound contact layer comprises a fluid interactive adhesive.

18. The method of claim 17 wherein the fluid interactive adhesive is a hydrocolloid adhesive.

19. The method of claim 1, wherein the absorbent material layer is fibrous.

20. The method of claim 1, wherein the backing layer is coated with a pressure sensitive adhesive.

21. The method of claim 1, wherein the backing layer is an occlusive film or foam.

22. The method of claim 1, wherein the backing layer is microporous.

23. The method of claim 1, wherein the steps (a)–(e) are carried out in a registered continuous process.

24. The method of claim 1 wherein step (c) further comprises die cutting and removing the matrix of the continuous web of absorbent material.

25. A wound dressing manufactured by the method of claim 1.

26. A method of manufacturing a multilayered wound dressing comprising a wound contact layer, an absorbent material layer and a backing layer, comprising:
   (a) providing a substantially continuous first web comprising the wound contact layer having a first and second major face and a first process release liner adhered to the first major face of the wound contact layer;
   (b) applying a discrete absorbent material layer from a substantially continuous web of the absorbent material layer to the second major face of the wound contact layer, wherein the absorbent material comprises a plurality of absorbent fibers;
   (c) laminating a substantially continuous web of the backing layer over the absorbent material layer to form the composite web;
   (d) applying pressure to the composite web sufficient to drive fibers of the absorbent material layer into the wound contact layer; and
   (e) cutting individual multilayered wound dressings from the composite web,
wherein the steps (a)–(e) are carried out in a continuous sequence.

* * * * *